United States Patent
Hansson

(10) Patent No.: US 6,322,547 B1
(45) Date of Patent: Nov. 27, 2001

(54) METHOD OF PRODUCING AN INTERMITTENT ELASTIC WEB

(75) Inventor: Roy Hansson, Molndal (SE)

(73) Assignee: SCA Molnlycke AB, Gothenburg (SE)

( * ) Notice: Subject to any disclaimer, the term of this patent is extended or adjusted under 35 U.S.C. 154(b) by 0 days.

(21) Appl. No.: 09/319,547

(22) PCT Filed: Nov. 21, 1997

(86) PCT No.: PCT/SE97/01958

§ 371 Date: Jul. 7, 1999

§ 102(e) Date: Jul. 7, 1999

(87) PCT Pub. No.: WO98/25767

PCT Pub. Date: Jun. 18, 1998

(30) Foreign Application Priority Data

Dec. 9, 1996 (SE) .................................................. 9604523

(51) Int. Cl.[7] .................................................. A61F 13/15
(52) U.S. Cl. .................................. 604/385.25; 604/385.26; 604/385.24
(58) Field of Search .................. 604/385.21, 385.25, 604/385.26, 385.27, 385.3, 385.23; 156/164, 271, 264, 265, 266

(56) References Cited

U.S. PATENT DOCUMENTS

| | | | |
|---|---|---|---|
| 4,617,082 | * 10/1986 | Oshefsky et al. | 156/447 |
| 4,915,767 | * 4/1990 | Rajala et al. | 156/440 |
| 5,147,487 | * 9/1992 | Nomura et al. | 156/164 |
| 5,236,539 | * 8/1993 | Rogberg et al. | 156/495 |
| 5,330,598 | * 7/1994 | Erdman et al. | 156/164 |
| 5,576,091 | * 11/1996 | Zajaczkowski et al. | 428/192 |
| 5,755,902 | * 5/1998 | Reynolds | 156/73.1 |
| 5,766,411 | * 6/1998 | Wilson | 156/495 |
| 5,797,895 | * 8/1998 | Widlund et al. | 604/385.2 |

FOREIGN PATENT DOCUMENTS

| | | | |
|---|---|---|---|
| 0 113 976 | 7/1984 | (EP) | A41B/13/02 |
| 0 170 922 | 2/1986 | (EP) | A41B/13/02 |
| WO 80/00676 | 4/1980 | (WO) | A41D/9/14 |

* cited by examiner

Primary Examiner—John G. Weiss
Assistant Examiner—Jacqueline F Stephens
(74) Attorney, Agent, or Firm—Young & Thompson

(57) ABSTRACT

A method of producing an intermittent elastic web of material. According to the invention, an elongated elastic element (1) is laid-out in a pre-stretched state and in a longitudinal extending wave form and is fastened to a longitudinally extending web (2) such that the web transversely touches or extends beyond the outermost part of wave crests (3) and wave troughs (4) of the wave-shaped elastic element (1), whereafter a longitudinal cut (C) is made in the web so that at least outer parts of wave crests and wave troughs are located on mutually opposite sides of the cut.

8 Claims, 3 Drawing Sheets

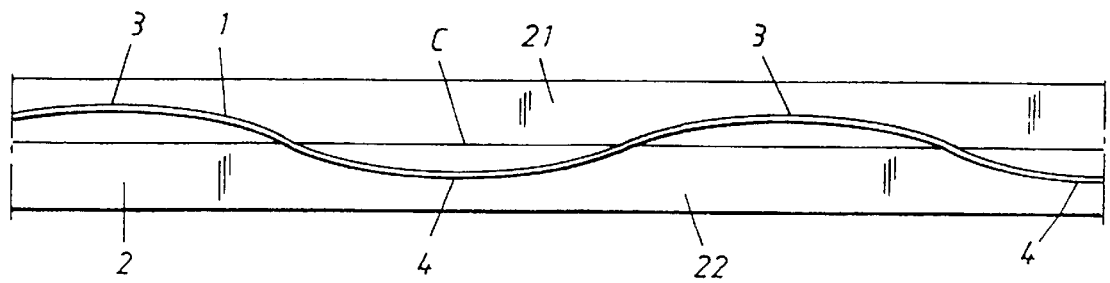

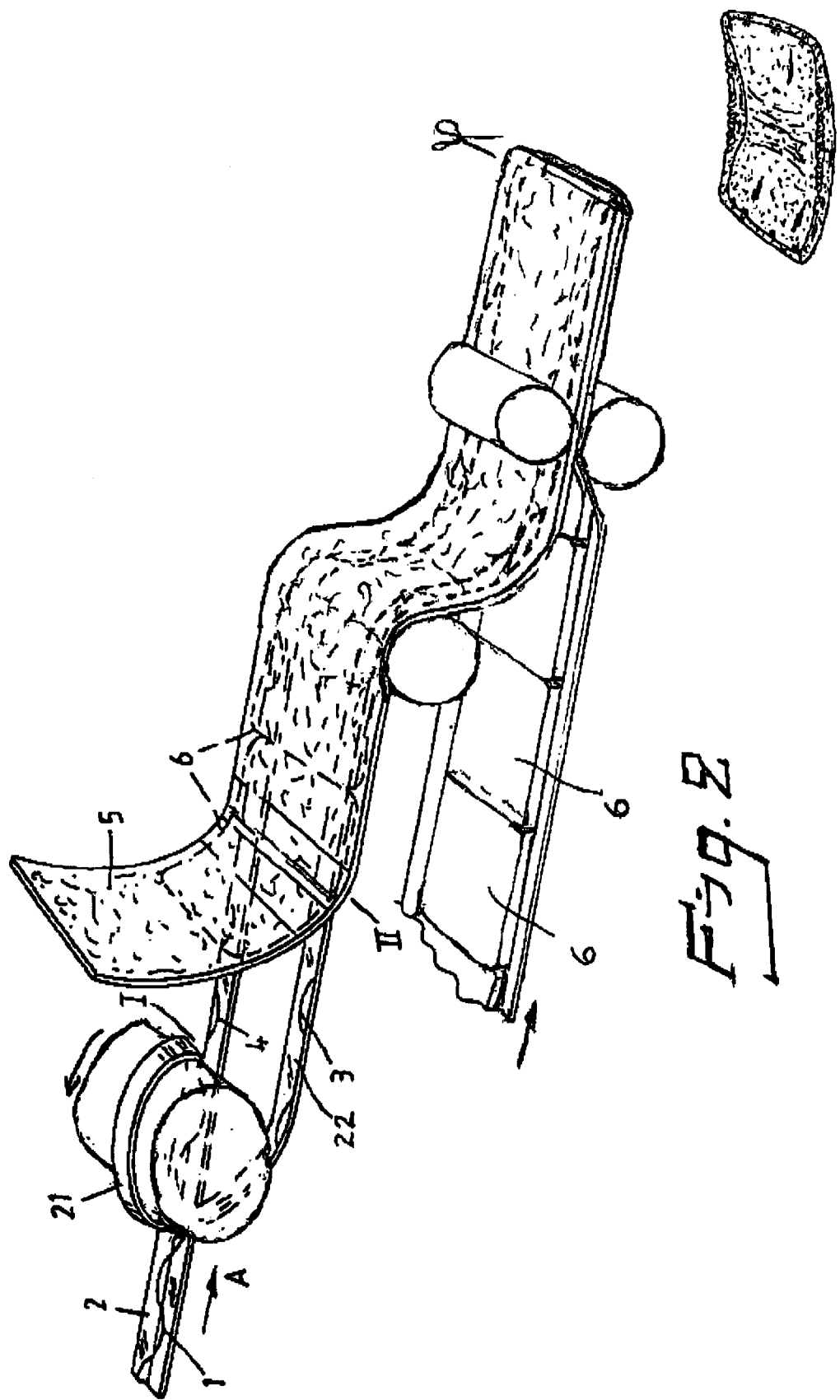

METHOD OF PRODUCING AN INTERMITTENT ELASTIC WEB

CROSS REFERENCE TO RELATED APPLICATION

This is the 35 USC 371 national stage of International Application PCT/SE97/01958 filed on Nov. 21, 1997, which designated the United States of America.

FIELD OF THE INVENTION

The present invention relates to a method of producing an intermittent elastic web of material, a method of applying elastic in the manufacture of absorbent sanitary articles, and a sanitary article provided with elastic in accordance with this latter method.

BACKGROUND OF THE INVENTION

For different reasons, it is normal to provide absorbent sanitary articles, such as sanitary napkins, diapers and incontinence guards, with elastic elements. For instance, diapers are nearly always provided with so-called leg elastic which functions to provide sealing abutment of the diaper casing sheet with the thighs of the wearer. Elastic elements are also often used to give sanitary articles or parts of such articles a desired shape, and also to provide waist elastic. Elastic is also used to raise liquid barrier forming parts of the article, to prevent liquid from spreading across the outer sheet of the article. Absorbent sanitary articles of the aforesaid kind are produced in a continuous process line, in which a web of material, that normally forms the outer backing sheet of the article, travels continuously through the process line in successive stages which include the application of absorbent bodies and the application of further surface sheets or layers and elastic elements. The individual articles are cut from the continuous composite web in the final stage of such a process line. The elastic elements are most often mounted in a pre-stretched state, i.e. have been stretched from a rest state to which they strive to return. So that the pre-stretched elastic elements will not contract and therewith gather together or pucker the material to which they are fastened, the elastic elements are maintained in a stretched state until the final stage of the manufacturing process. This can be readily achieved with elastic elements that extend across the full length of the article in the movement direction of the process line. However, in the case of elastic elements that are active across only a part of the length of the article in the movement direction, a problem arises in retaining the elements in a pre-stretched state without complicating the process and/or without mounting functionally inactive parts of elastic elements on the web in the article manufacturing process. A solution to this problem is proposed in Swedish Patent Application No. 9602131-6 filed on May 31, 1996.

OBJECT OF THE INVENTION

The present invention aims to solve these problems in a simpler manner than that proposed in the aforesaid patent application.

SUMMARY OF THE INVENTION

In accordance with the invention, this object is achieved by means of a method of producing an intermittent elastic web which is characterized by laying-out an elongated elastic element in a pre-stretched state in a longitudinally extending undulating or wave shape and fastening said element to a longitudinally extending web of material in a manner such that the web touches or extends transversely beyond the outermost parts of the wave crests and wave troughs of the undulating elastic element, and thereafter cutting a longitudinal section from the web such as to divide the web into two parts in which at least outer parts of wave crests and wave troughs will be located on opposite sides of the cut longitudinal section. This will result in two intermittent elastic webs which, in the continuous production of absorbent sanitary articles, can be caused to extend along the full length of the article in the direction of web movement, while enabling associated severed wave-shaped parts of the elastic element to be placed in intended positions on the article. Because the severed wave-shaped parts are fastened in a stretched state to a continuous carrier, there is no difficulty in keeping the carriers, and therewith the elastic elements, in a stretched state up to the final stage of manufacture.

In one preferred embodiment, the elastic element is laid-out in a regular wave form and the cut parts of the web are displaced longitudinally in relation to one another by an odd multiple of half the wave length, so that wave crests and wave troughs will be located opposite one another in the longitudinal direction.

The invention also relates to a method of applying elastic in the manufacture of absorbent sanitary articles, said method being characterized by laying-out an elongated elastic element in a regular longitudinal wave-shape and fastening said element to a longitudinally extending web of material having a first and a second long edge, such that the web transversely touches or extends beyond the outermost parts of wave crests and wave troughs of the wave-shaped elastic element, and thereafter taking-out a longitudinal section from the web such that wave crests and wave troughs will be located on opposite sides of the section that is taken-out and such that the web will be divided into two parts, of which one part is displaced transversely in relation to the other part so that, subsequent to said displacement, both web parts will extend parallel with one another with the first and second edges of the web facing towards each other, and also displacing said parts longitudinally by an odd multiple of half a wave length, wherein the two web parts are thereafter fastened to a casing sheet or to an absorbent body of an absorbent sanitary article with wave crests and wave troughs located in the crotch part of the article.

According to one preferred embodiment in which the elastic is applied to blanks from which absorbent sanitary articles are produced and which are disposed sequentially in a continuous row on a travelling conveyor belt with their longitudinal axes coincidin with the direction of belt movement, the wave length of the elastic element is chosen to be equal to the length of the absorbent sanitary article.

The invention also relates to an absorbent sanitary article, such as a sanitary napkin, a diaper or an incontinence guard, that includes two elastic elements which oppose one another in relation to the longitudinal axis of the article, wherein said article is characterized in that the elastic elements are fastened to wave-shaped carriers that have straight edges, in that said carriers are fastened to the article in general and extend along the full length of the article, and in that the elastic elements are arcuate in shape with their ends facing towards the nearest adjacent long edge of the article and extend over a distance which is equal to half the length of said article.

BRIEF DESCRIPTION OF THE DRAWINGS

The invention will now be described in more detail with reference to the accompanying drawings, in which FIG. 1 illustrates schematically two intermittent elastic webs produced in accordance with a preferred embodiment of the invention;

FIG. 2 illustrates schematically the various stages of fastening intermittent elastic webs to a sanitary napkin casing sheet in accordance with one preferred embodiment of the invention;

DESCRIPTION OF THE PREFERRED EMBODIMENTS

Figure 3:
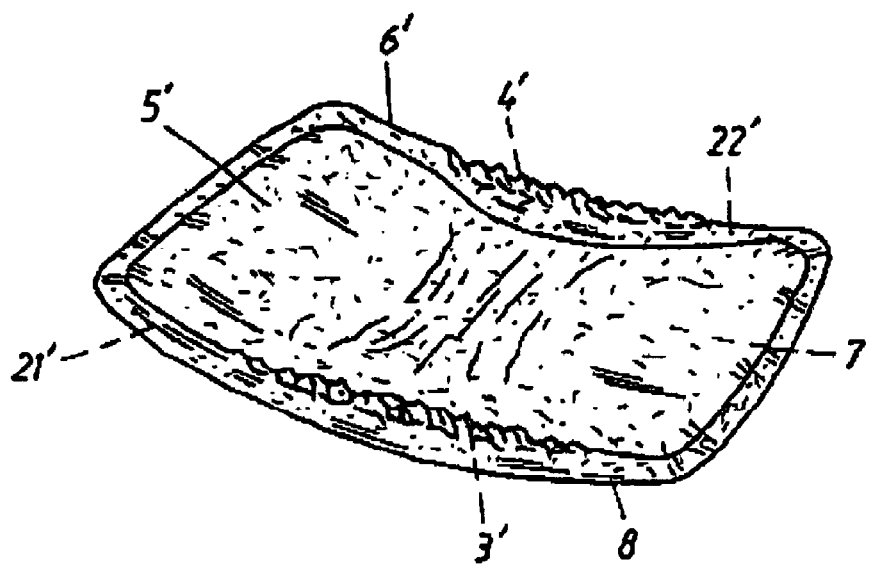
FIG. 3 is a perspective view of a sanitary napkin according to a preferred embodiment of the invention.

FIG. 1 illustrates schematically the various stages in the manufacture of an intermittent web. A pre-stretched elastic thread 1 is laid on a web 2 in a first stage of manufacture and fastened to the web in some suitable way. For instance, a second web of material can be placed on top of the first web and fastened thereto by ultrasound welding or by gluing such as to secure the thread between the two webs. Alternatively, the thread may be fastened directly to the web 2. The methods in which elastic threads can be laid-out and secured are well known to the person skilled in this art and do not constitute any part of the present invention.

According to the present invention, the thread 1 is laid-out in an undulating path having wave crests 3 and wave troughs 4. In the illustrated example, the thread is laid in a regular sinusoidal path that has a relatively small amplitude. However, the thread may be laid-out in other undulating configurations, e.g. square wave configurations. Neither is it necessary for the undulating configuration to be regular and the wave length and amplitude can be varied if so desired.

An intermittent elastic web is produced by dividing the web 2 carrying the thread 1 into two webs 21, 22 by means of a longitudinally extending cut C, which cuts the sinusoidal thread 1 at those points at which wave crests merge with wave troughs. The resultant webs 21, 22 are intermittently elastic by virtue of the web 21 including a row of elastic thread sections 3 separated by half a wave length and comprising the wave crests of the laid-out thread 1, while the web 22 includes a row of separated elastic thread sections 4 that comprise the wave troughs of the laid-out thread 1.

FIG. 2 is a schematic illustration of how the afore-described method can be applied as a part of a sanitary napkin production line. Those components shown in FIG. 2 that find correspondence with components in the FIG. 1 illustration have been identified by the same reference numerals. A continuous web 2 carrying a sinusoidally shaped elastic thread 1 is advanced in the direction marked A in FIG. 2. When the web 2 reaches a cutting device (not shown) at location I, the web is cut along its longitudinal axis into two web portions or slices 21, 22, each of which includes mirror-symmetrical thread sections 3, 4. These thread sections 3, 4 are displaced longitudinally relative to one another through one-half wavelength at the location I, i.e. in the web movement direction. The web portion 21 moves obliquely around a roller such as to be displaced transversely over and beyond the web portion 22, which continues in the direction of web movement from the location I without being displaced. After the web portion 21 has left the roller, it moves in the movement direction parallel with the web portion 22 and in space relationship therewith. The diameter of the roller over which the web portion 21 runs has a diameter such as to displace the web portion 21 through a distance corresponding to an odd multiple of half a wavelength in relation to the web portion 22 during its passage over the roller. This means that the elastic thread sections 3 and 4 on the web portions or slices 21, 22 will move transversely opposite one another subsequent to the web portion 21 leaving the roller.

When the parallel moving web portions 21, 22 reach the location II in the process line, a web of material 5 is placed over the 25 web portions 21, 22 and fastened thereto in some suitable fashion, e.g. by ultrasound welding or gluing. The web 5 is comprised of a material suitable for use as the liquid-permeable casing sheet of a sanitary napkin, e.g. a nonwoven material or perforated plastic film. The composite web comprised of the web portions 21, 22 and the web 5 is then transported in a manner not shown to a conveyor or the like that carries a continuous web of material suitable for the liquid-impervious outer sheet of a sanitary napkin, e.g. a plastic film. This continuous web carries a row of absorbent bodies, and the composite web 21, 22, 5 shown in FIG. 2 is placed on and fastened to the web carrying said absorbent bodies, with the web portions 21, 22 facing towards said web. Individual sanitary napkins are then cut from this web. FIG. 2 shows in broken lines the contour 6 of those sanitary napkins that are cut from the continuous web of sanitary napkin blanks in the final stage of the described manufacturing process. It will be observed that the webs 2, 21, 22, 5 and the web carrying the absorbent bodies are typically maintained in a stretched state during the whole of the manufacturing process up to the final stage in which the sanitary napkins are cut from the web.

In order for the mutually sequential pairs of elastic thread sections 3, 4 carried by the web portions 21, 22 to be positioned correctly in the sanitary napkins that are cut-out in a later stage of the manufacturing process, it is necessary for the wavelength of the sinusoidal thread 1 to be equally as long as the sanitary napkin that is cut out. It will be understood that after dividing the web 2 into said web portions 21, 22 the spacing between said web portions can be varied and chosen in accordance with where the thread sections 3, 4 shall be placed on the following absorbent sanitary article in the direction of web movement.

FIG. 3 is a schematic, perspective view of a sanitary napkin manufactured in the manner illustrated in FIG. 2. Those components in FIG. 3 that find correspondence with components in the FIG. 2 illustration have been identified with the same reference signs as those used in FIG. 2 but with the addition of a prime. The sanitary napkin illustrated in FIG. 3 typically includes an absorbent body 7 enclosed between a liquid-permeable outer sheet 5' and a liquid-impervious outer sheet 8. The outer sheets 5', 8 protrude peripherally beyond the absorbent body 7 and are joined together at these protruding parts. Web portions 21', 22' that carry elastic threads 3', 4' which extend in the crotch part of the article are introduced between the outer casing sheets along the long-edge parts of the sanitary napkin. FIG. 3 shows the sanitary napkin in the relaxed state in which it is removed from its package. As will be seen from FIG. 3, the thread sections 3', 4' have contracted so as to raise those parts of the outer sheets 5', 8 of the napkin that extend laterally outside the absorbent body. This contraction of the elastic threads 3', 4' also causes the absorbent body to curve slightly in a longitudinal direction in the crotch part of the sanitary napkin.

Figure 4:
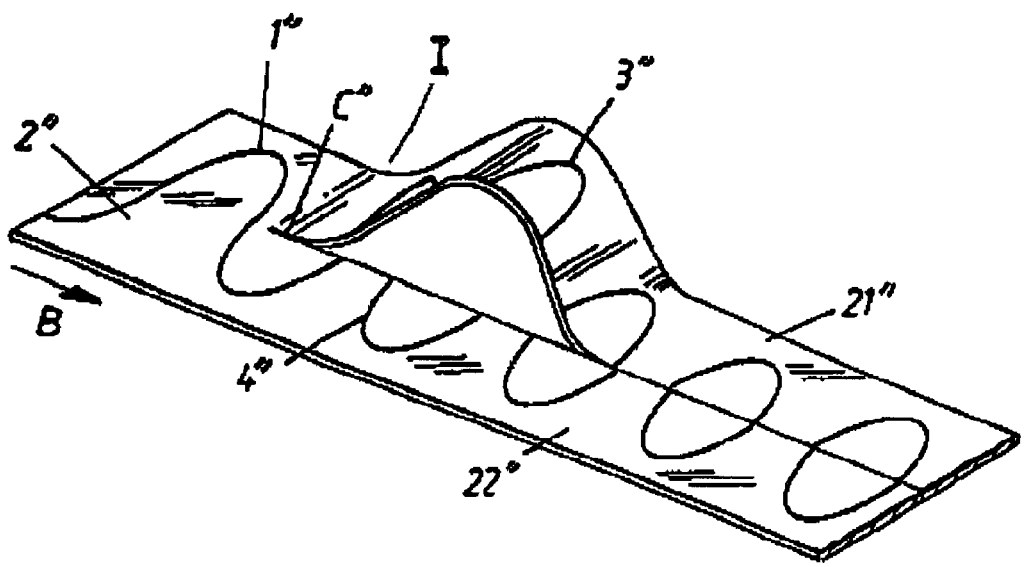
FIG. 4 illustrates schematically various stages in the manufacture of intermittent elastic webs in accordance with a second embodiment of the invention.

FIG. 4 illustrates schematically how the method described with reference to FIG. 1 can be readily applied to provide on a carrier sheet, layers with elastic that is laid out in the form of an intermittent row of ellipses or circles. Those components in the FIG. 4 illustration that find correspondence in the FIG. 2 illustration have been identified with the same reference signs to which a double prime has been added. Thus, the left part of FIG. 4 shows a web 2" on which an elastic thread 1" has been placed in a regular undulating pattern and moved in the direction of arrow B by a conveyor not shown. As the web passes the location I" a middle cut C" is made in the web 2" so as to divide the web into two web portions 21", 22". The web portion 21" includes a row of wave crests 3" that are mutually separated by half a wavelength. After passing the location I", the web portion 21" is passed over a roller (not shown) of such diameter as to displace the web portion 21" through half a wavelength relative to the web portion 22" in the longitudinal direction, whereafter the web portion 21" is returned to the conveyor carrying the web portion 22". The wave crests 3" of the web portion 21" will therewith be located opposite the wave troughs 4" in the row of wave troughs of the web portion 22", said row being produced by cutting at the location I" as earlier described. The web portions 21" and 22" are then moved side-by-side and edge-to-edge by the conveyor and can be fastened to a row of absorbent bodies carried by a travelling web on an underlying conveyor. The width of the web 2" is adapted to the desired use of the web. For instance, if the web is to be used as an outer sheet of an absorbent article, the web 2" will have the same width as the web that carries the aforesaid absorbent bodies.

Alternatively, the web portions 21", 22" can be offset transversely in relation to one another at an earlier stage, so that said web portions slightly overlap when the web portion 21" is returned to the conveyor from the aforesaid roller. The mutually overlapping parts of the web portions 21", 22" are then fastened together in some suitable manner, for instance by gluing or welding, so as to obtain a coherent web that includes intermittent rows of circular elastic. The coherent web can be rolled up onto a storage reel or, as before mentioned, applied directly to an underlying web for the manufacture of absorbent sanitary articles. Such a web can be used to obtain perforated top sheets for absorbent sanitary articles with elastic extending around the holes, by punching-out material located inwardly of the circles of elastic elements.

In order to ensure that severed ends of elastic threads do not project out beyond the cut edges of the carrier web, it may be suitable to refrain from fastening the elastic thread to a longitudinally extending part along the contemplated cutting line, when laying-out the elastic thread. The non-fastened ends of the elastic thread will then contract to a relaxed state as the web is cut. This is particularly suitable in those instances when the carrier web is comprised of two layers with the thread sandwiched therebetween. When producing a coherent web having a longitudinally central overlapping part in the aforedescribed manner, it may also be convenient to utilize the aforesaid contraction effect of non-fastened end-parts of elastic threads to produce an overlapping part in which no elastic threads are present.

The web 2, 2" is conveniently comprised of a liquid permeable nonwoven material, although other materials may alternatively be used, such as perforate or imperforate plastic film.

It will be evident from the method illustrated in FIG. 2 that discrete longitudinally extending elastic elements can be applied very readily in the continuous production of absorbent sanitary articles without complicating the manufacturing process and without spillage or wastage of elastic material. The method is highly suitable for applying leg elastic to diapers or incontinence guards. The method can also be applied conveniently in respect of transversely extending, discrete elastic elements in the transverse production of such articles, i.e. when the transverse direction of the article blanks coincide with the direction of movement.

It will be understood that the aforedescribed embodiment can be modified within the scope of the invention. For instance, the web 2 can be given a greater width so as to enable the web portions cut from the web to move edge-to-edge subsequent to offsetting either of these web portions laterally and longitudinally. This embodiment enables the outer sheet 5 indicated in FIG. 2 to be omitted, provided that the web 2 is comprised of a soft and skin-friendly material. The elastic element may consist of an elastic band or the like, instead of the illustrated elastic thread. Neither is it necessary for the longitudinal cut C to be symmetrical in relation to the laid-out thread. For instance, the cut may be asymmetrical when wishing to produce web-like carriers with rows of elastic thread sections of mutually different lengths and mutually different spacings therebetween. It is also possible to use curved cuts in order to vary thread lengths and spacing between thread sections on one and the same carrier. It is also conceivable to fasten the web portions 21, 22 in FIG. 2 directly to an absorbent body of a sanitary article, particularly when the web portions 21, 22 are given a width which enables said portions to form one of the outer sheets of the article. The invention is therefore restricted solely by the contents of the following claims.

What is claimed is:

1. A method of producing an intermittent elastic web of material, which comprises:
    laying out an elongated elastic element in a pre-stretched state in a longitudinally extending wave shape having wave crests and wave troughs;
    fastening the elastic element to a longitudinally extending web such that the web will transversely touch or extend beyond outermost parts of the wave crests and the wave troughs of the elastic element; and
    thereafter making a longitudinally extending straight cut in a longitudinal direction of the web such that at least the outer parts of the wave crests and wave troughs will be located on mutually opposite sides of the cut on two different cut portions.

2. The method according to claim 1, wherein the elastic element is laid out in a regular wave form.

3. The method according to claim 2, further comprising displacing the cut portions of the web longitudinally in relation to each other by an odd multiple of half a wavelength, so that the wave crests and wave troughs are located opposite one another in the longitudinal direction.

4. The method according to claim 1, wherein the elastic element is left unfastened to the web within a web region along a contemplated cutting line.

5. A method of applying elastic in the manufacture of absorbent sanitary articles, which comprises:
    laying out an elongated elastic element in a regular, longitudinally extending wave form having wave crests and wave troughs;
    fastening the elastic element to a longitudinally extending web having a first and a second long edge, such that the web will transversely touch or extend beyond outermost parts of the wave crests and the wave troughs of the elastic element;
    thereafter making a longitudinal straight cut in the web so that the wave crests and the wave troughs are located on mutually opposite sides of the cut, and so that the web will be divided into two web portions, wherein one web portion is offset transversely in relation to the other web portion;

offsetting said web portions in a longitudinal direction by an odd multiple of half a wavelength, so that subsequent to said offsetting, both web portions extend parallel to each other with the first and second long edges of the web facing towards one another; and fastening the two web portions to an outer sheet or an absorbent body of an absorbent sanitary article with the wave crests and wave troughs located in a crotch part of said article.

6. The method according to claim 5, wherein the elastic element is applied to an outer sheet of absorbent sanitary articles that are produced sequentially in a continuous row on a conveyor traveling in a conveying direction with longitudinal axes of said articles coinciding with the conveying direction, and wherein the elastic element has a wavelength which is chosen to equal a length of the absorbent sanitary article.

7. The method according to claim 5, wherein the elastic element is left unfastened to the web within a web region along a contemplated cutting line.

8. An absorbent sanitary article selected from the group consisting of a sanitary napkin, a diaper and an incontinence guard, and comprising:

two elastic elements on mutually opposite sides of a longitudinal axis of the article;

said elastic elements being fastened to web carriers having straight edges;

said carriers being fastened to the article in general and extending along a full length of the article; and said elastic elements being arcuate and having ends, which face towards a nearest delimiting longitudinal edge of the article and extend over a length which is equal to half the length of the article.

* * * * *